(12) United States Patent
Beecham

(10) Patent No.: US 10,978,205 B1
(45) Date of Patent: Apr. 13, 2021

(54) ROBOTS, SOCIAL ROBOT SYSTEMS, FOCUSING SOFTWARE DEVELOPMENT FOR SOCIAL ROBOT SYSTEMS, TESTING AND USES THEREOF

(71) Applicant: James E. Beecham, West Palm Beach, FL (US)

(72) Inventor: James E. Beecham, West Palm Beach, FL (US)

( * ) Notice: Subject to any disclaimer, the term of this patent is extended or adjusted under 35 U.S.C. 154(b) by 0 days.

(21) Appl. No.: 17/075,213

(22) Filed: Oct. 20, 2020

Related U.S. Application Data

(63) Continuation-in-part of application No. 17/033,190, filed on Sep. 25, 2020, and a continuation-in-part of
(Continued)

(51) Int. Cl.
*B25J 11/00* (2006.01)
*B25J 9/16* (2006.01)
(Continued)

(52) U.S. Cl.
CPC ............. *G16H 40/63* (2018.01); *G06Q 50/01* (2013.01); *G16H 10/20* (2018.01)

(58) Field of Classification Search
CPC ........ G06N 20/00; G06N 3/008; G06N 3/006; G06N 3/08; G06N 3/0454; G06N 3/0445;
(Continued)

(56) References Cited

U.S. PATENT DOCUMENTS 9,724,824 B1 * 8/2017 Annan ................. B25J 11/0005
10,452,816 B2 * 10/2019 Kidd ...................... G16H 40/63
(Continued)

OTHER PUBLICATIONS

Pinto et al., Users' Perception Variance in Emotional Embodied Robots for Domestic Tasks, 7 pages (Year: 2018).*
Chen et al., Reverse Engineering Psychologically Valid Facial Expressions of Emotion into Social Robots, 5 pages (Year: 2018).*

*Primary Examiner* — Thuy Dao
(74) *Attorney, Agent, or Firm* — Christopher Pilling

(57) ABSTRACT

A method and system for improving the software programming of a robot system, comprising monitoring of plurality of human user-robot interactive pairs' (HURIP) interactions. System comprises each of said plurality of HURIPs as using 'front-end' semi-autonomous robot component linked by wireless two-way communications to a 'back-end' cloud-based computerized component. Monitoring comprises review of robot sensor-gathered data and data from camera and audio data from homes of users during user-robot interactions. Analysis of said monitoring by authorized observers such as psychologist, parent, teacher, system administrator, software programmer(s), enables identification of areas for software improvement. Improved software is tested, wherein testing comprises at least similar monitoring of HURIPs, and wherein said testing comprises social robots comprising said updated software. Cycles of such monitoring of HURIP interactions, analyzing data derived from said monitoring, focus for improvement derived thereof and followed-up in coding updates, testing of updates comprising use within monitored HURIP interactions, such cycles are applied in herein disclosed method to manufacture progressively improved code for and uses of social robot system.

18 Claims, 5 Drawing Sheets

Related U.S. Application Data application No. 17/026,666, filed on Sep. 21, 2020, and a continuation-in-part of application No. 17/070,671, filed on Oct. 14, 2020.

(51) Int. Cl.

| | | |
|---|---|---|
| *B25J 9/00* | (2006.01) | |
| *B25J 13/00* | (2006.01) | |
| *G06N 3/00* | (2006.01) | |
| *G16H 40/63* | (2018.01) | |
| *G16H 10/20* | (2018.01) | |
| *G06Q 50/00* | (2012.01) | |

(58) Field of Classification Search
CPC .......... H04L 67/12; A63F 13/35; A63F 13/12; A63F 13/215; A63F 13/216; B25J 11/0005; B25J 11/001; G16H 40/63; G16H 40/67; G16H 10/20; G06Q 50/01
See application file for complete search history.

(56) References Cited

U.S. PATENT DOCUMENTS

| | | | |
|---|---|---|---|
| 2013/0211587 A1* | 8/2013 | Stephens, Jr. | B25J 9/1689 700/246 |
| 2015/0199561 A1* | 7/2015 | Jeong | G06K 9/00288 382/118 |
| 2016/0199977 A1* | 7/2016 | Breazeal | B25J 9/1694 700/246 |
| 2018/0091933 A1* | 3/2018 | Ling | G06F 16/5866 |
| 2018/0144236 A1* | 5/2018 | Tan | H04L 51/32 |
| 2018/0287968 A1* | 10/2018 | Koukoumidis | G06F 16/248 |
| 2019/0108770 A1* | 4/2019 | Fischer | G09B 19/00 |
| 2019/0245812 A1* | 8/2019 | Rico | B25J 9/0003 |
| 2019/0262990 A1* | 8/2019 | Grollman | B25J 9/163 |
| 2019/0361672 A1* | 11/2019 | Odhner | B25J 9/1697 |
| 2019/0389064 A1* | 12/2019 | High | B25J 13/08 |
| 2019/0392003 A1* | 12/2019 | Zweig | G06N 3/008 |
| 2020/0159648 A1* | 5/2020 | Ghare | G06F 8/33 |
| 2020/0276707 A1* | 9/2020 | Go | G06F 9/548 |
| 2020/0306988 A1* | 10/2020 | Shaffer | B25J 13/082 |

\* cited by examiner

Same Initial Model Robots
- Translation
- Family videos
- School/culture
- Cosmetics

Coordinate switch to advanced model
- Progress togeather to teenage years
- Replay childhood shared videos
- Prizes and community activities
- Parental controls

FIG. 3

ROBOTS, SOCIAL ROBOT SYSTEMS, FOCUSING SOFTWARE DEVELOPMENT FOR SOCIAL ROBOT SYSTEMS, TESTING AND USES THEREOF

CROSS-REFERENCE TO RELATED APPLICATION

The present invention claims priority to non-provisional application Ser. No. 17/033,190 filed 25 Sep. 2020 by instant inventor, entitled ROBOT SYSTEM AND ASSOCIATED CONTROL OF INTERNET OF THINGS DEVICES AND FUNCTIONS hereby incorporated in its entirety at least by reference; and the present invention claims priority to non-provisional application Ser. No. 17/026,666 filed 21 Sep. 2020 by instant inventor, entitled CO-ADAPTATION OF HUMAN BEING AND ARTIFICIAL INTELLIGENCE-ENABLED ROBOT-LINKED SYSTEM, AND METHOD FOR SYSTEM MANUFACTURE hereby incorporated in its entirety at least by reference; and the present invention claims priority to non-provisional application Ser. No. 17/070,671 filed 14 Oct. 2020 by instant inventor, entitled SOCIAL ROBOT SYSTEM WITH USER-SELECTED EXCHANGE OF ROBOT HABITUS FRONT-END AND COMMON/CONTINUOUS BACK-END SUPPORT OF CLOUD-LINKED COMPUTER hereby incorporated in its entirety at least by reference.

FIELD OF THE INVENTION

The instant invention generally relates to social robot system. More specifically, instant invention relates to monitoring of human user-robot interactions to identify focus for software improvement for social robot system.

BRIEF SUMMARY OF THE INVENTION

As background, the first autonomous robots (ARs), i.e. robots capable of operating independently from human operators, were designed to tackle potentially hazardous tasks, often far from people. These ARs explored deep oceans, the interiors of volcanoes and the surface of Mars. The next generation of ARs will have to do something even more difficult, i.e. fit into everyday human life.

Designing robots that can interact with people in homes, schools, hospitals, and workplaces is a serious scientific challenge. Designers will need to draw from psychological research in areas such as communication, perception, social-emotional intelligence, and theory of mind. Understanding people is only half the equation. Developers also need to consider what features robots will need to possess so that people trust them and want to engage with them.

The instant invention comprises at least one solution to at least one of the above disclosed problems. In a preferred embodiment, a plurality of human users, each using and interacting with a 'front-end' semi-autonomous robot component linked by wireless two-way communications to the same 'back-end' cloud-based computerized component, have their interactions monitored. Such monitoring comprises means to derive and analyze data which brings into focus areas needing improvement within social robot system, such as improved software for improved social robot performance.

In instant invention, the term human user-robot interactive pair (HURIP) means one human user interacting with one front-end robot, said front-end robot wirelessly linked to a first back-end cloud computer component. In instant invention, the term as a plurality, i.e. HURIPs, is defined as one human user interacting with one front-end robot, said front-end robot wirelessly linked to a first back-end cloud computer component plus another human user interacting with another front-end robot, this second front-end robot also wirelessly linked to same back-end. In instant invention, identifying a focus for software development is defined to mean finding an area of the robot system software which, if improved, will improve the interactions and scope for interactions of users and robots within the system.

In a preferred embodiment, said front-end social robots comprise humanoid social robots selected from a plurality of robot habitus 'front-end' configurations linkable to unified back-end cloud component. The social robots herein disclosed comprise those disclosed in U.S. non-provisional application Ser. No. 17/070,671 by same inventor, cited above. Please refer to that disclosure for details.

In a preferred embodiment, the interaction environment of a plurality of human user-robot pairs (HURIPs) is individually monitored by separate camera(s) and microphone(s). Such separate camera and microphone are typically within the home dwelling of the human users, typically attached to a wall of the room wherein said user interacts with said robot.

In a preferred embodiment, the feeds of the said separate cameras and microphones are enabled, such as by internet VPN connection, to be available to authorized human observers/monitors to review and comment with suggestions to system administrator or the like. It is understood that the robot system comprises all the needed hardware and software to enable the functionalities herein disclosed.

In a preferred embodiment, a plurality of HURIPs are observed in interactions, such as daily interactions, such observations enabled for analysis by the feeds of data from the robot sensors, and by the feeds of data from the separate room-mounted cameras and microphones. In essence, the various homes of the said HURIPs under such monitoring comprise a living laboratory, one in which a goal is to enable improvements in social robot software performance within the system by focusing via monitoring on observed areas needing improvement.

In a preferred embodiment, said HURIP interactions comprise interactions within each pair, and interactions between one pair and the other pair, and interactions between one user to a second user, and interactions of one social robot to a second social robot. In a preferred embodiment, the authorized human observers/monitors of said HURIP interactions comprise at least one of list: psychologist, parent/grandparent, software programmer, system administrator, teacher.

In a preferred embodiment, such observations and monitoring comprise online, real time interactions and/or review of recorded sessions of interaction. In a preferred embodiment, said observations and monitoring comprise a testbed for testing newly coded software programming as uploaded into the system from time to time, such updates coded to satisfy observed/identified needs for improvement. In a preferred embodiment, monitoring-derived data is analyzed, comprising use of at least one of list: algorithms, artificial intelligence, image analysis, speech recognition, collating, statistical analysis, and the like.

In a preferred embodiment, a psychological questionnaire and/or IQ test is administered to at least one user, such as prior to beginning interactive sessions, or after a period of interaction sessions. In a preferred embodiment, said questionnaire can be of the OCEAN type, i.e. multi-question format used to categorize a person as to personality traits of openness to experience, conscientiousness, extraversion, agreeableness, and neuroticism. The results of said psychological questionnaire are employed within the system. For example, the questionnaire results can be used to assign a HURIP to use of a special type of software, the testing of which helps to verify such software version works best for a particular personality type of user. Such personality type can be a highly intelligent or highly inquisitive user, or an outgoing user, or an introverted user, or the like. For example, a user with questionnaire results suggesting social shyness can receive a trial with software coded to enable more effective robot interaction with a shy user. In a preferred embodiment, user personality is determined by analyzing said user's social network communications and characteristics, with such data similarly applied within robot system of instant invention.

In a preferred embodiment, monitored reactions of a user are recorded as to newly introduced programming for the robot system, such as programming introduced in accord to user personality as based on questionnaire and/or IQ test results and/or social network communications and characteristics of user. The interactions are analyzed and used to comprise changes as needed in said software program focus for software development. In a preferred embodiment, said correlation enables selection of software content for at least one group of users, such as shy users per psychological questionnaire results.

In a preferred embodiment, a first human user interaction with autonomous robot under monitorship within instant invention system, comprises deriving data correlating interactions of said first HURIP user with a second HURIP user. Where such monitoring reveals an idea derived from observing the said two users, an idea about improving their mutual robot interaction experiences can occur. Mention of idea by observer to system administrator enables coding of system software to respond to said idea focus for programming.

In a preferred embodiment, computerized analysis of user-robot interactions and user-user interactions and robot-robot interactions herein, such analysis comprises use of artificial intelligence. In a preferred embodiment, a monitored link between users comprises wireless two-way communications, including monitoring the robots' responses to users. In a preferred embodiment, where said responses of robots do not maximize the expected quality of interactions, software focus on corrective coding is thus identified.

In a preferred embodiment, the monitoring personnel, i.e. one or more of psychologist, parent/grandparent, software programmer, system administrator, teacher, or the like, are enabled access to data of user interactions. In a preferred embodiment, said interaction-related data is collated (collected and combined in proper order) and statistically analyzed, such as for level of interaction interest of user(s), level of emotion displayed by user(s), reaction by robot(s) as to responsiveness to user(s), and the like. It is understood that the robot system comprises all the needed hardware and software to enable the functionalities herein disclosed.

In a preferred embodiment, among the plurality of front-end robot body styles available to users for linking to back-end cloud component, are annual updated versions. In preferred embodiment, annual update front-end robot habitus bodies comprise year-by-year more advanced models. In a preferred embodiment, such annual update versions are designed by psychologist/software programmer teams to provide age-appropriate models. Such model comprise software updates derived from coding to the focus for software development identified in monitoring of HURIPs as herein disclosed.

In a preferred embodiment, standard age-appropriate front-end annual updates are tested on users of various personality types. For example, a conscientious six-year-old child could use the six-year-old childhood most conscientious robot level front-end during her sixth year of life, then exchange it for similar most conscientious seven-year-old child robot front-end on her $7^{th}$ birthday.

In a preferred embodiment, monitoring observers can comprise a teacher, such as the teacher of at least one of the users of HURIPs. For example, a teacher can review, either in real time online, or in recorded video review, the interactions of said child in her class as child is interacting with his robot. In a preferred embodiment, teacher can advise the programmers of needs of child on which to focus coding updates. In a preferred embodiment, such advice is comprised in software upgrade to said child's robot.

In a preferred embodiment, teacher can send to robot the files regarding homework. In a preferred embodiment, parent can speak to robot and elicit the files on homework, such as assignment information, tutor availability, her individual child's needs and performance, and the like.

In a preferred embodiment, user is instructed in method for teaching his robot. In a preferred embodiment, robot is programmed to respond to certain instructions, such as by making a movement of robot arm in response to user speaking a command, or user demonstrating the movement of human arm which robot will mimic. In a preferred embodiment, user is instructed to share his success in teaching his robot a behavior, by sharing related knowledge to other users in other human user-robot interactive pairs.

In a preferred embodiment, each user learns to teach his robot at least one of several new robot behaviors. In a preferred embodiment, at the request of an interacting second user, a first user teaches the said requesting second user how to teach his robot a new robot behavior. In a preferred embodiment, the behavior taught by the user to his robot is how to play a game, such as pong, a computer version of tennis. In a preferred embodiment, the first user shows the second user how the robot can be taught to play pong. In a preferred embodiment, when both robots have learned to play pong, the system is enabled by software programming to have the first user-robot pair play the second user-robot pair in a game of pong in a contest for prizes.

In a preferred embodiment, such game of pong play comprises first user striking the pong 'ball' displayed on his robot display screen, then the other pair's human user taking a turn on his robot's screen. In a preferred embodiment, then the first user's robot takes a turn, and then the second user's robot takes a turn. Other game play is envisioned, including awarding of prizes within HURIP community. In a preferred embodiment, said community comprises linking of at least a dozen of HURIPs.

In a preferred embodiment, the users are from different parts of the world, and they speak different native languages. In a preferred embodiment, the system is enabled to translate native languages, so that when one user hears the other user, each hears the other as translated to their native language. In a preferred embodiment, each user hears the words of the other user and the words of both robots in the user's native language.

In a preferred embodiment, the users are enabled via the system, to leave messages for each other via their robots, and to send video clips from their robot's camera recordings. In a preferred embodiment, said sending of video clips comprises sending clip to other robot of system, whereby other user can view playing on robot-mounted display. In a preferred embodiment, the monitoring observers are enabled to provide feedback to system administration, to include notations and referenced video clip as example for where to focus software updates. In a preferred embodiment, testing of updates comprises monitoring related HURIP interactions.

In a preferred embodiment, a plurality of software programmers via links are enabled to code for system improvement using open source code system. In a preferred embodiment, at least one user is enabled to use a software developers kit (SDK) to code update for the software of his own robot.

As background, the following publications are herein incorporated in their entirety, at least by reference:

U.S. Pat. No. 10,430,744 to Look, regards a community of robots and users to perform tasks, and U.S. Pat. No. 9,124,447 to Goodman, regards a robot user (program application) that represents the community of users but appears to the community as simply another user, and U.S. Pat. No. 4,974,191 to Amirghodsi, regards computer translation between a natural language, such as English to another natural language, and U.S. Pat. No. 10,300,606 to Florencio, regards adapting robot behavior based upon human-robot interaction, and U.S. Pat. No. 9,846,843 to Howard, regards methods and systems for facilitating interactions between a robot and user, and U.S. Pat. No. 9,724,824 to Annan, regards sensor use and analysis for dynamic update of interaction in a social robot, and U.S. Pat. No. 9,375,845 to Annan, regards synchronizing robot motion with social interaction, and U.S. Pat. No. 8,909,370 to Stiehl, regards interactive systems employing robotic companions, and U.S. Pat. No. 6,038,493 to Tow, regards affect-based robot communication methods, and U.S. Pat. No. 10,052,769 to Houssin, regards robot capable of incorporating natural dialogues with a user into the behaviour of same, and U.S. Pat. No. 9,950,421 to Monceaux, regards humanoid game-playing robot, method, and system for using said robot U.S. Pat. No. 10,265,227 to Wen, regards mobile human-friendly assistive robot, and U.S. Pat. No. 9,789,605 to Meier, regards training robots to perform custom tasks by generating control commands derived from the sensory data, and U.S. Pat. No. 8,095,238 to Jones, regards modular robot development kit includes programmable development module, and U.S. Pat. No. 10,691,514 to McClory, regards system and method for integration, testing, deployment, orchestration, and management of applications, and U.S. Pat. No. 10,318,412 to McKearney, Jr., regards systems, methods, and apparatus for dynamic software generation and testing, and U.S. Pat. No. 9,740,752 to Nowak, regards determining user personality characteristics from social networking system communications and characteristics, and U.S. Pat. No. 7,966,093 to Zhuk, regards robot-to-human conversational interface and provide on-the-fly translations of situational requirements into adaptive behavior.

BRIEF DESCRIPTION OF THE FIGURES

Other features and advantages of the present invention will become apparent when the following detailed description is read in conjunction with the accompanying drawings, in which:

FIG. 3 is a chart of a preferred embodiment.

DETAILED DESCRIPTION OF PREFERRED EMBODIMENTS

Figure 1:
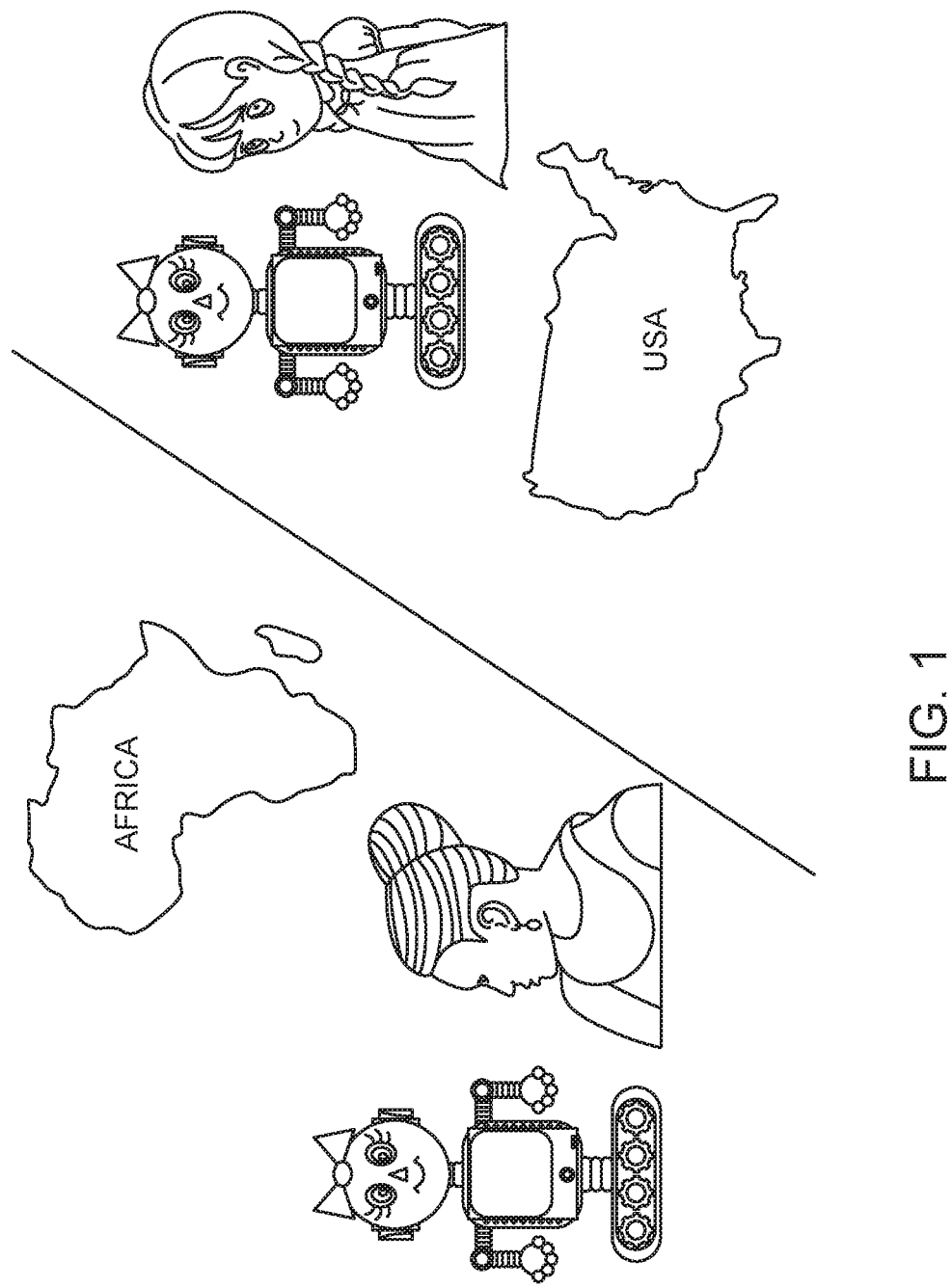
FIG. 1 is an illustration of a preferred embodiment comprising a first human user-robot interactive pair on one continent, and a linked second human user-robot interactive pair on second geographic continent.

In FIG. 1, a preferred embodiment of instant invention is illustrated comprising a monitored environment for developing improved social robots. The environment comprises a plurality of sites of human user-robot interactions in different time zones of the Earth. In Africa, a home is outfitted with cameras/microphones linked to the internet. Within the home, a human user has a personal social robot of the system to interact with. This human user-robot interactive pair from Africa (left side of illustration) has a connection via the robot system to a second human user-robot interactive pair (HURIP) located in USA (right side of illustration). Daily interactions occur as time zones permit, such as early morning for HURIP in USA and late evening for HURIP in Africa. For example, the two girls learn about each other via mutual interactions with each other and their robots. The robots are programmed to enable these two girls to send messages and share videos, robot to robot. The audio of one robot can be heard by both users during their interactive sessions. The video of each robot display can be viewed on other robot video display during their interactive sessions. The girls teach the robots, such as by girls giving voice commands and/or making gestures. The girls have simplified SDKs by which they can implement simple programming upgrades to their robots and show each other the results. One girl can teach the other how to use their simplified software developer kits (SDKs). The robots teach the girls also, such as by step-by-step how-to videos played on the robot screens. Among these videos are the lessons demonstrating how these robot functions work. The girls teach each other, such as by one girl telling the other how to use voice commands to enable her robot to interact with herself. Monitoring interactions of the girl user-robot interactive pairs (HURIPs) provides advice from observers suitable to focus software development. Such software updates benefit the functionality of the system and user satisfaction. Analysis of said monitoring by authorized observers such as psychologist, parent, teacher, system administrator, software programmer(s), enables identification of areas for focused software improvement. For example, if the girl users state a wish that the system could do some function, that is a means of identifying areas for software improvement. For example, if the girl users have difficulty making a function work, that is observed by monitor, and can become a focus for software update. Such means of identifying areas for software improvement, for testing such improved software, for testing of software update, and monitoring use thereof, such process comprises feedback cycles for improving social robot function. For example, where robot system's translation into native language is not intelligible, user comments focus software programming to strengthen the translation function. Subsequent monitoring confirms improved translation capability is either achieved or requires further update coding.

During the interactions, each girl speaks her own language. The robot system translates from language to language so that the girls hear the words from the other girl translated to their native language. The girls each have a relationship to their robot. Their personal robot is learning to relate more effectively to each girl via artificial intelligence within system. One girl can show the other girl how her robot does interactions, such as dancing or laughing or calling the housecat or the like. The girl learns the possibilities.

Figure 2:
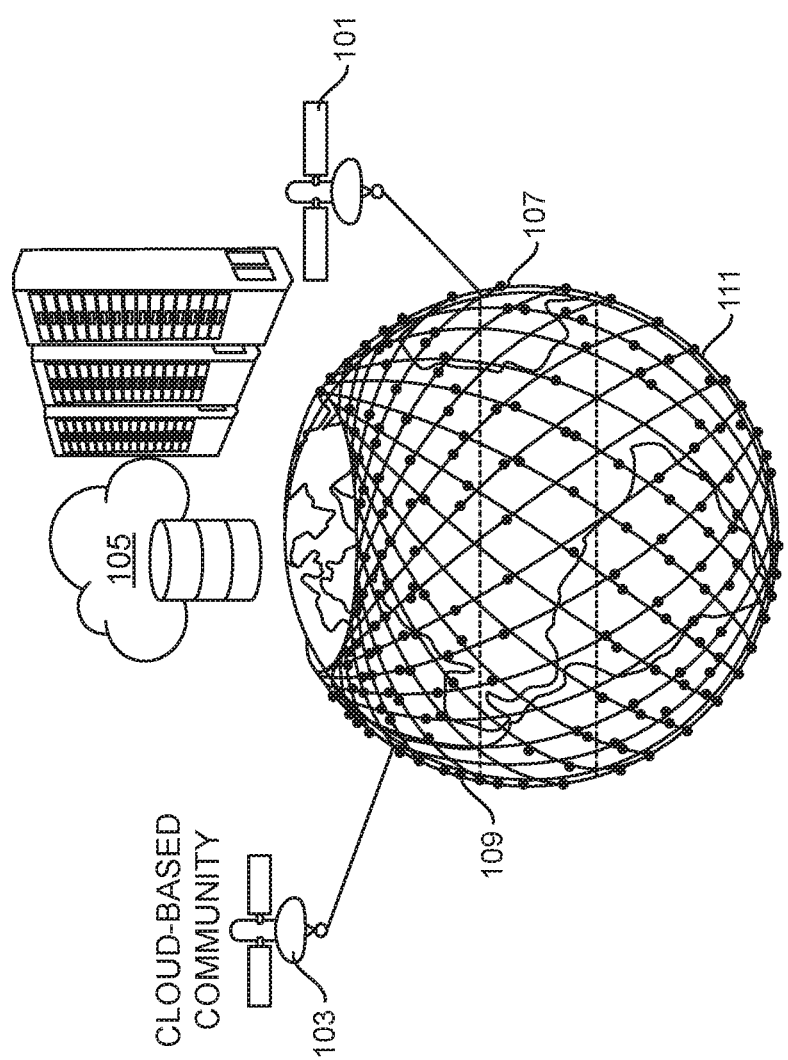
FIG. 2 is an illustration of a preferred embodiment comprising use of a low earth orbit satellite communication system.

In FIG. 2, a preferred embodiment of the robot system is illustrated wherein the FIG. 1 HURIP from Africa communicates via low earth orbit satellite system (111) using ground-based transceiver (107) to and from satellite (101). The HURIP from USA communicates via low earth orbit satellite system using ground-based transceiver (109) to and from satellite (103). These satellite communications are linked to a ground-based processing center, a 'cloud' component to which each HURIP is linked (105). With low latency of communications time, the low earth orbit satellite communications enable robot interactions for HURIPs to be conversational, i.e. flows well with little discernable delay, thus being generally comparable in flow to a normal conversation flow. Although illustrated here for two pair of HURIP, instant system, it is understood that the system comprises capacity for hosting many thousands of HURIPs.

In FIG. 3, a preferred embodiment of instant invention is illustrated comprising a chart disclosing aspects of system. The robots comprise two-way wireless communications to the cloud computer function, as well as communications to and from and between HURIPs of community. Thus, the system is a living laboratory for development and testing of new software for the system. For the girl users interacting to their personal robots, the girls are able to set the system so it translates their girl to girl conversations as well as translating the first HURIP robot's words into language of second HURIP girl's native tongue. Thus, each girl can understand the other girl, and each girl can understand what her own and the other robots are saying. The girls are enabled to share videos over the robot to robot link, such that one girl's family videos can play for the other girl on her own robot's screen. Similarly, the girls can share each other's school activities and culture, by music and/or live video. Girls can they take their robot to class, or the like, and record interactions. Similarly, the girls can practice cosmetic make-up application, to themselves as well as to their respective robot. The girls can share the results of their make-up practice on video to each other. In a preferred embodiment, girls can improve the sharing by putting their own robot in front of a mirror, recording a video via wall-mounted camera, then sending that video to the other girl's robot, so that mirror video can be played on the display of the second girl's robot.

In a preferred embodiment, the girls decide to exchange/upgrade their own robot's front-end components at the same time. In this way, on her $9^{th}$ birthday in Africa, a first user gets a new 'Model Nine' front-end robot to interact with, and contemporaneously her girlfriend in USA nearing her own $9^{th}$ birthday, gets her own new 'Model Nine' front-end robot. In this manner, the girls progress in their learning together, such as learning how to program their robots via the SDKs. Thus, the girls progress together to their teenage years, still using their personal robots in annual update front-ends, as learning and socialization tools. The girls can reminisce about childhood shared memories by calling up video of the event on their respective robot screen. The girls can share video to the other girl via her robot. The girls can involve other HURIPs in their respective community. The robot system can compete for prizes in contests open to all HURIPs.

Figure 4:
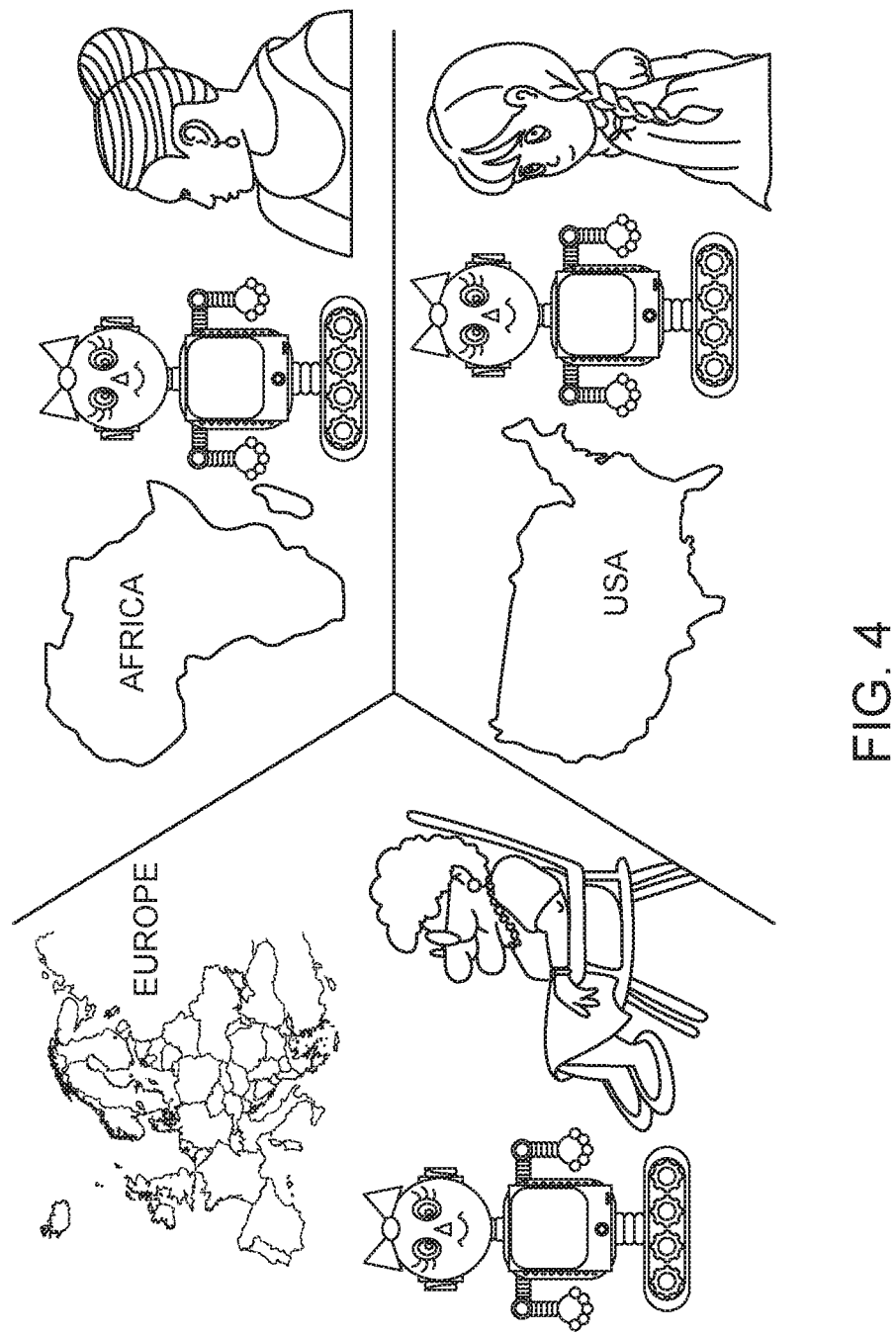
FIG. 4 is a schematic of a preferred embodiment comprising robot-human user interactive pairs under monitorship.

In FIG. 4, the HURIPs of FIG. 1 are illustrated in a preferred embodiment. By system authorization, monitoring of the interactions of the HURIPs is enabled, such as for grandmother (illustrated as monitoring from Europe), parent, psychologist, teacher, or the like. The purpose of said monitoring comprises enjoyment for grandmother in seeing her grand-daughter happy. The purpose can also comprise assessment of the system functionality, with monitor/observer enabled to offer suggestions for improvement, and the like.

Figure 5:
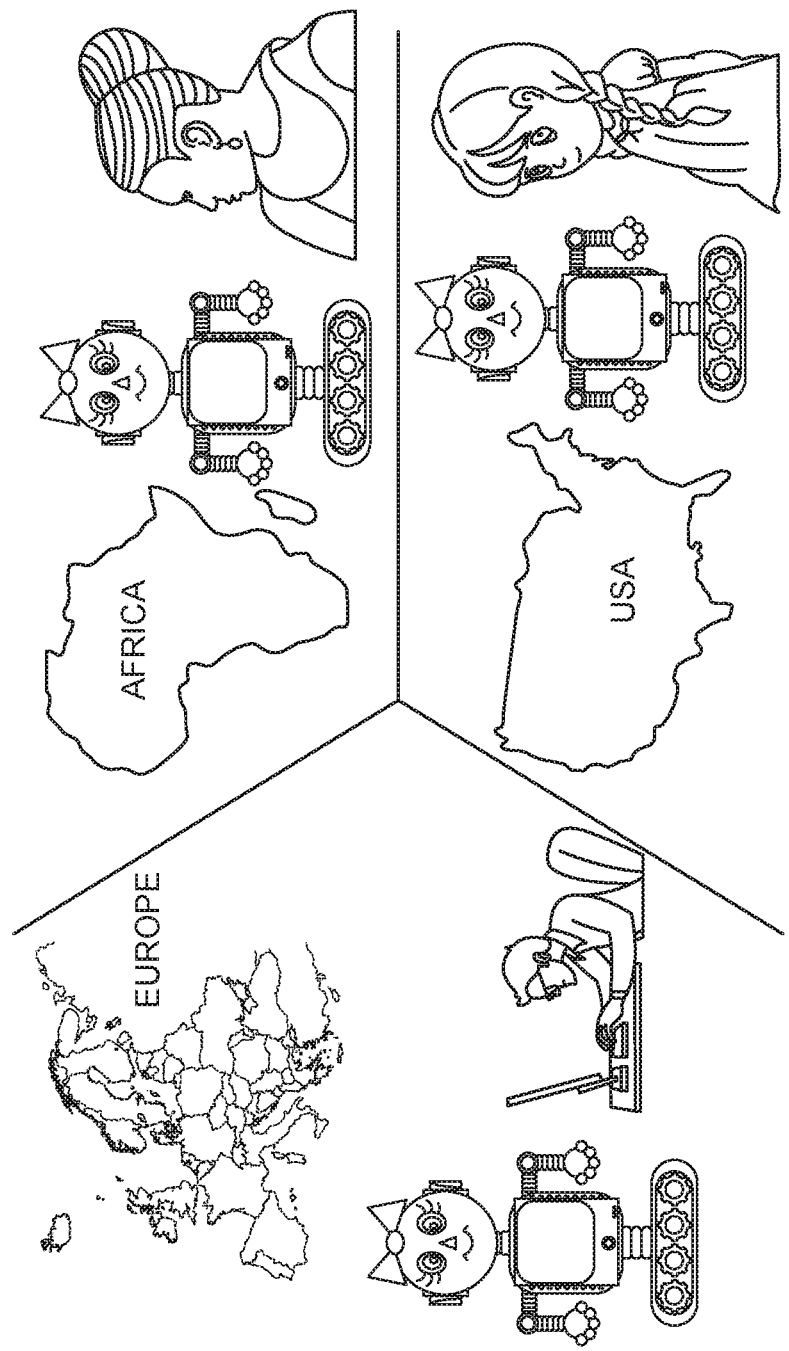
FIG. 5 is a schematic of a preferred embodiment comprising robot-human user interactive pairs under monitorship.

In FIG. 5, the HURIPs of FIG. 1 are illustrated in a preferred embodiment. By system authorization, monitoring of the interactions of the HURIPs is enabled, such as for computer programmers of the system. The purpose of said monitoring typically comprises assessment of the system software functionality, suggestions for code improvement, and the like. The illustration depicts the double system for viewing available to the computer programmer. The robot display and speaker is enabled to play/replay the interactions occurring in the robots of the HURIPs. The separate computer screen computer programmer is viewing is enabled to play the video feed and audio feed of the camera/microphone wall-mounted in homes of each of the two girls, typically presented for review on a split screen view for the programmer. Similar double viewing is available by permission to other monitors, such as parent, grandparent, system administrator, teacher, psychologist, or the like. Code updates are thus derived by software programmers who also can monitor testing. Testing of updated code comprises at least similar monitoring of HURIPs and analysis thereof, and wherein robot system operates using said code update developed by said programmer(s). Testing is designed to verify improved functional improvement of social robots when said robots execute software version comprising said code update. Cycles of focus-finding, coding and testing comprise such monitoring of HURIP interactions, with analyzing of data derived from said monitoring, deriving a focus for improvement, coding the improvement, applying update in system, and following-up in testing coded updates comprising use within monitored HURIP interactions. Such cycles are progressively applied in herein disclosed method to manufacture progressively improved code for social robot system.

Although the invention has been described in considerable detail in language specific to structural features, and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated and can be made without departing from the spirit and scope of the invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

What is claimed is:

1. A social robot system comprising process of using audio and video sensors to compile data of remote monitoring of in-home interactions of at least a first pair in a first home comprising a first human user interacting with a first robot, and interactions in a second home of a second pair comprising a second human user interacting with a second robot, said video data at least comprising perspective view wherein both robot and user are in frame during at least one user-robot interaction and said video data further comprising at least one view of user facial expression during said same perspective view interaction, and said process further comprised of analysis of said data comprising at least comparison of interactions, said compared interactions comprising at least those of one of robot and user of said first pair interacting with at least one of robot and user of said second pair via system communication connections, before the update, as compared to interactions via system communication connections comprising at least those of one of robot and user of said first pair interacting with at least one of robot and user of said second pair after the update is applied within system, wherein update is continued in system provided success proven by said analysis.

2. The social robot system and process of claim 1 further comprising analysis of data gathered from interactions of user-robot pairs from different geographic time zones of the world wherein said users and robots mutually interacted simultaneously.

3. The social system and process of claim 1 further comprising gathering of data of robot-robot interplay.

4. The social system and process of claim 1 further comprising enablement of conversational timing in user-user and user-robot interactions, such timing enabled via use of low-earth orbit satellite.

5. The social system and process of claim 1 further comprising interaction wherein community of users and their robots participate in prospect of winning prize.

6. The social system and process of claim 1 further comprising interaction wherein cosmetics are applied to robot.

7. The social system and process of claim 1 further comprising interaction wherein at least one how-to-video on robot training is viewed simultaneously by at least plurality of users.

8. The social system and process of claim 1 further comprising use of artificial intelligence at least in analysis of data.

9. A method for enabling user-robot pairs from different geographic time zones of the world to mutually and agreeably interact simultaneously, said method comprising step of using in-home mounted audio and video sensors to gather data regarding interactions of at least a first pair of human user with his robot and a second pair comprised of human user with her robot, said method further comprising within said gathered video data at least one perspective view of user-robot interaction wherein both robot and user of interacting pair are in frame, and at least contemporaneous view of at least one of that user's facial expressions at time of said perspective view user-robot interaction, said method further comprising use of said data in identification of at least one target for software update within system, said method further comprising step of measuring update success as to quality of interactions enabled via at least one target-identified software update, wherein update is continued in system provided success proven by said analysis.

10. The method of claim 9 further comprising step of using artificial intelligence in process of said analysis.

11. The method of claim 10 further comprising using low earth orbit satellite in process of communication of said data.

12. The method of claim 9 further comprising step of gathering of data of robot-robot interplay.

13. The method of claim 9 further comprising step of enabling conversational timing in interactions, such timing enabled via use of low-earth orbit satellite.

14. The method of claim 9 further comprising step of users and their robots participating in prospect of winning prize.

15. The method of claim 9 further comprising step of applying cosmetics to robot.

16. The method of claim 9 further comprising step of receiving by a user of new robot equipment appropriate in outward appearance to user's recently reached age.

17. The method of claim 9 further comprising step of using at least one how-to-video.

18. The method of claim 9 further comprising step of using artificial intelligence.

* * * * *